(12) United States Patent
Anderle

(10) Patent No.: US 11,306,709 B2
(45) Date of Patent: Apr. 19, 2022

(54) DIAPHRAGM PUMP DEVICE AND DIAPHRAGM PUMP HAVING A DIAPHRAGM PUMP DEVICE AND AN ACTUATION DEVICE

(71) Applicant: FRESENIUS MEDICAL CARE DEUTSCHLAND GMBH, Bad Homburg (DE)

(72) Inventor: Jens Anderle, Deggingen (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 203 days.

(21) Appl. No.: 16/470,562

(22) PCT Filed: Dec. 19, 2017

(86) PCT No.: PCT/EP2017/083665
§ 371 (c)(1),
(2) Date: Jun. 18, 2019

(87) PCT Pub. No.: WO2018/115028
PCT Pub. Date: Jun. 28, 2018

(65) Prior Publication Data
US 2019/0345925 A1 Nov. 14, 2019

(30) Foreign Application Priority Data
Dec. 21, 2016 (DE) .................. 10 2016 015 206.0

(51) Int. Cl.
*F04B 43/073* (2006.01)
*A61M 60/268* (2021.01)
(Continued)

(52) U.S. Cl.
CPC ......... *F04B 43/073* (2013.01); *A61M 60/268* (2021.01); *F04B 43/028* (2013.01);
(Continued)

(58) Field of Classification Search
CPC ...... F04B 43/073; F04B 49/065; F04B 49/22; F04B 43/06–0733; F04B 43/028; A61M 60/268; F16K 7/14–17
(Continued)

(56) References Cited

U.S. PATENT DOCUMENTS 2,383,193 A 8/1945 Herbert
3,154,021 A * 10/1964 Vick, Jr. ............. F04B 43/1133
417/394
(Continued)

FOREIGN PATENT DOCUMENTS

CN 101354029 A * 1/2009
CN 101354029 A 1/2009
(Continued)

OTHER PUBLICATIONS

International Search Report and Written Opinion issued in corresponding International Patent Application No. PCT/EP2017/083665 (with English translation of International Search Report) dated Mar. 27, 2018 (15 pages).

(Continued)

*Primary Examiner* — Alexander B Comley
(74) *Attorney, Agent, or Firm* — Kilyk & Bowersox, P.L.L.C.

(57) ABSTRACT

The invention relates to a membrane pump device 2 for conveying fluids, in particular medical liquids for blood treatment. The invention furthermore relates to a membrane pump with a membrane pump device 2 and an actuating device 1 for the membrane pump device 2. The membrane pump device 2 has a pump chamber body 253 in which a recess, which is closed by an elastic membrane 201 to form a pump chamber 252, is constructed. The membrane pump device 2 moreover comprises an inward flow path 219 which connects an entry connection 204 to an inlet opening 215 of (Continued)

Figure 1:
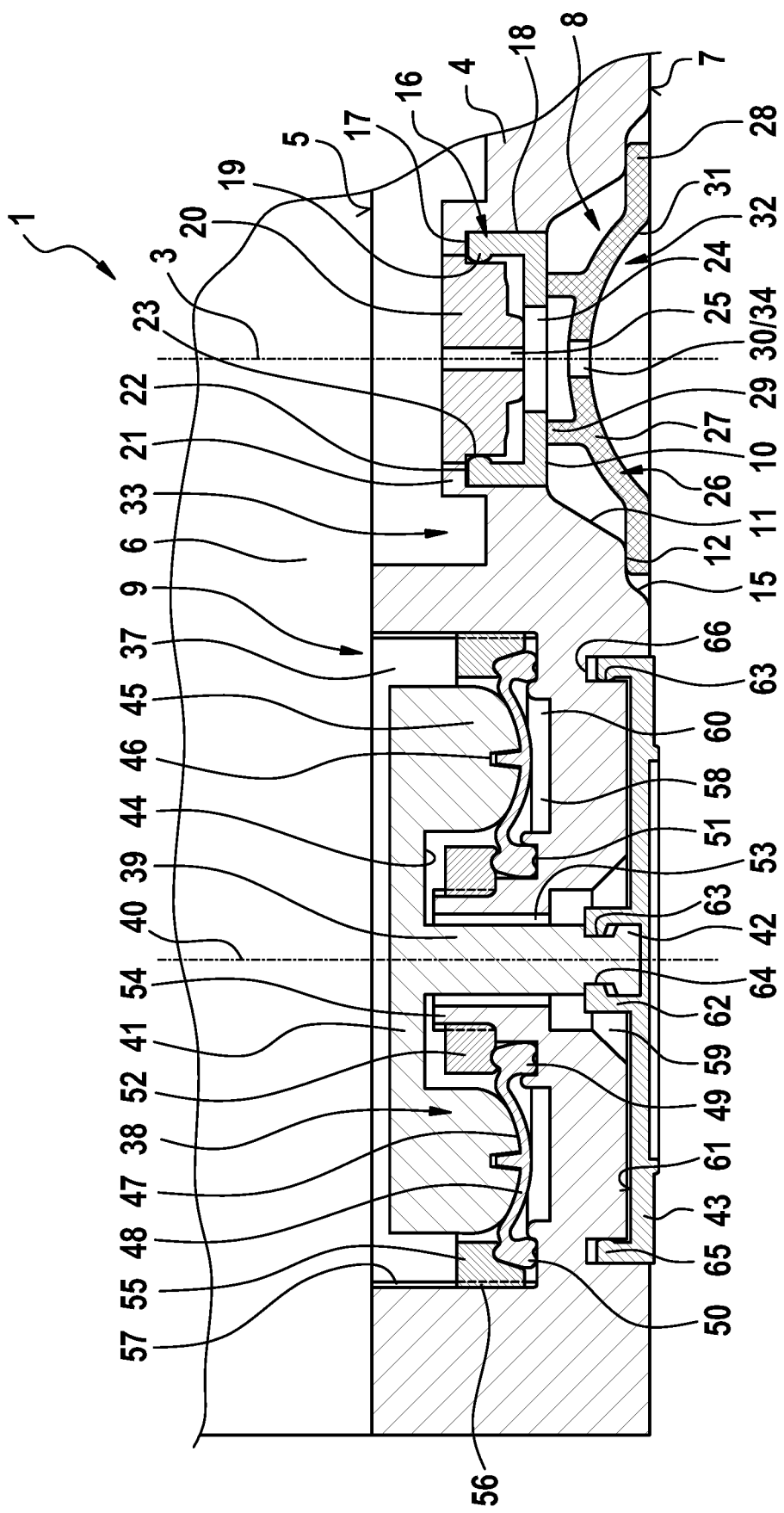

the pump chamber 252, and an outward flow path 223 which connects an outlet opening 216 of the pump chamber 252 to an exit connection 205. An inlet valve 202 is provided in the inward flow path 219 and an outlet valve 203 is provided in the outward flow path 223. The outlet valve 203 is a membrane valve which has a valve body 254A in which a recess is constructed which is closed by an elastic membrane 201 to form a valve chamber 218 in which a valve seat 225 is arranged, the front face of which faces the membrane and in the open position of the outlet valve is arranged at a distance from the valve seat, wherein a valve channel 240 passes through the valve seat. The outward flow path 223 comprises a first outward flow channel 214 which connects the outlet opening 216 of the pump chamber 252 to the outlet valve chamber 218, and a second outward flow channel 214A which connects the outlet valve chamber 240 to the exit connection 205, wherein the cross-section area of the outlet valve channel 240 is smaller than the cross-section area of the region of the valve chamber 218 surrounding the outlet valve seat 225.

16 Claims, 7 Drawing Sheets

(51) Int. Cl.
  *F04B 43/06* (2006.01)
  *F04B 49/06* (2006.01)
  *F04B 49/22* (2006.01)
  *F04B 43/02* (2006.01)
(52) U.S. Cl.
  CPC ............ *F04B 43/06* (2013.01); *F04B 49/065* (2013.01); *F04B 49/22* (2013.01)
(58) Field of Classification Search
  USPC .......................... 417/395; 137/538, 540, 542
  See application file for complete search history.

(56) References Cited

U.S. PATENT DOCUMENTS

| | | | | |
|---|---|---|---|---|
| 3,357,360 A * | 12/1967 | Borell | ................... | F04B 43/073 417/390 |
| 3,689,204 A * | 9/1972 | Prisk | ..................... | F04B 43/025 417/394 |
| 4,050,859 A | 9/1977 | Vork | | |
| 4,158,530 A * | 6/1979 | Bernstein | ............ | F04B 43/1133 417/389 |
| 4,276,004 A | 6/1981 | Hahn | | |
| 4,290,346 A * | 9/1981 | Bujan | ................. | F04B 43/0054 417/478 |
| 4,479,762 A * | 10/1984 | Bilstad | .................. | A61M 1/306 417/395 |
| 4,583,920 A * | 4/1986 | Lindner | .............. | F04B 43/0733 417/266 |
| 4,646,781 A * | 3/1987 | McIntyre | .............. | A61M 39/24 137/512.4 |
| 5,076,890 A * | 12/1991 | Balembois | ........... | G05D 7/0635 162/198 |
| 5,088,515 A * | 2/1992 | Kamen | ................. | F16K 31/005 137/15.17 |
| 5,195,986 A * | 3/1993 | Kamen | ................. | A61M 5/162 604/251 |
| 5,252,041 A * | 10/1993 | Schumack | ........... | F04B 43/073 417/395 |
| 5,499,909 A * | 3/1996 | Yamada | ................ | F04B 43/043 417/384 |
| 5,593,290 A * | 1/1997 | Greisch | ................ | F04B 43/021 417/478 |
| 5,725,363 A * | 3/1998 | Bustgens | .............. | F04B 43/043 417/413.1 |
| 5,857,661 A | 1/1999 | Amada et al. | | |
| 6,033,191 A * | 3/2000 | Kamper | ................ | F04B 43/043 417/322 |
| 6,520,753 B1 * | 2/2003 | Grosjean | ................. | F04B 19/24 417/379 |
| 7,284,966 B2 * | 10/2007 | Xu | ........................ | F04B 53/106 417/395 |
| 7,763,453 B2 * | 7/2010 | Clemmens | .......... | B01F 13/0059 435/286.7 |
| 7,832,429 B2 * | 11/2010 | Young | ................. | F16K 99/0055 137/829 |
| 8,038,640 B2 * | 10/2011 | Orr | ...................... | A61M 60/148 604/6.11 |
| 8,292,594 B2 * | 10/2012 | Tracey | .................... | F04B 23/06 417/43 |
| 8,323,586 B2 * | 12/2012 | Zhou | ................. | B01L 3/502715 422/502 |
| 2004/0019313 A1 | 1/2004 | Childers et al. | | |
| 2009/0137940 A1 | 5/2009 | Orr | | |
| 2013/0032210 A1 * | 2/2013 | Johnstone | ............. | F04B 19/006 137/1 |
| 2013/0058805 A1 * | 3/2013 | Chien | ................. | F04B 43/1133 417/395 |
| 2013/0178752 A1 * | 7/2013 | Kodama | ................ | F16K 15/145 600/498 |
| 2015/0217050 A1 * | 8/2015 | Dudar | ................... | A61M 5/172 604/500 |

FOREIGN PATENT DOCUMENTS

| | | |
|---|---|---|
| DE | 2826033 C2 | 4/1982 |
| DE | 19720482 A1 | 11/1998 |
| JP | H5-502096 A | 4/1993 |
| JP | 8-128389 A | 5/1996 |
| JP | 2006161779 A | 6/2006 |
| WO | 9013795 A | 11/1990 |
| WO | 2013110906 A1 | 8/2013 |
| WO | 2013110919 A1 | 8/2013 |

OTHER PUBLICATIONS

International Preliminary Report on Patentability issued in corresponding International Patent Application No. PCT/EP2017/083665 dated Jun. 25, 2019 (7 pages).
First Office Action dated Oct. 26, 2021, issued by the Japan Patent Office for Japanese Patent Application No. 2019-533379, and English-language translation (13 pages total).

* cited by examiner

DIAPHRAGM PUMP DEVICE AND DIAPHRAGM PUMP HAVING A DIAPHRAGM PUMP DEVICE AND AN ACTUATION DEVICE

This application is a National Stage Application of PCT/EP2017/083665, filed Dec. 19, 2017, which claims priority to German Patent Application No. 10 2016 015 206.0, filed Dec. 21, 2016.

The invention relates to a membrane pump device for conveying fluids, in particular medical liquids for blood treatment. The invention moreover relates to a membrane pump with a membrane pump device and an actuating device for the membrane pump device.

Membrane pumps are used in medical technology for conveying medical liquids. The advantage of membrane pumps lies in the drive unit being separated by a membrane from the fluid to be conveyed.

High requirements are imposed on membrane pumps in medical technology. For certain uses the membrane pumps should have a high conveying accuracy even at low flow rates. A particularly accurate metering at a low flow rate is required, for example, for citrate anticoagulation (CiCa anticoagulation) in dialysis.

Membrane pumps which have a membrane pump device intended only for a single use are known. The membrane pump device of these membrane pumps can be constructed as a disposable cassette, in which a recess closed by an elastic membrane is constructed. During the suction phase the fluid flow from the pump chamber is interrupted, and during the pressure phase the fluid flow into the pump chamber is interrupted. The elastic membrane can be driven with an actuating device which is not intended for a single use.

The invention is based on the object of developing a membrane pump of the construction described above such that the membrane pump allows a particularly accurate metering of fluids, for example a solution for CiCa anticoagulation, even at very low flow rates, wherein a constant fluid mass flow is to be ensured. In particular, the invention is based on the object of improving the conveying accuracy of the membrane pump device of such a membrane pump.

A further object of the invention is to provide a blood treatment apparatus, in particular a dialysis apparatus, with a membrane pump which allows a particularly accurate metering of a fluid, for example a solution for CiCa anticoagulation, with a constant fluid mass flow even at very low flow rates.

These objects are achieved according to the invention with the features of the independent claims. The dependent claims relate to advantageous embodiments of the invention.

The membrane pump device according to the invention has a pump chamber body in which a recess which is closed by an elastic membrane to form a pump chamber is constructed. The membrane pump device moreover comprises an inward flow path which connects an entry connection to an inlet opening of the pump chamber, and an outward flow path which connects an outlet opening of the pump chamber to an exit connection. An inlet valve is provided in the inward flow path and an outlet valve is provided in the outward flow path in order to be able to influence the flow of liquid in the inward flow and, respectively, outward flow path.

The invention relates in particular to the configuration of the outlet valve on the pressure side of the membrane pump device. In the membrane pump device according to the invention the outlet valve is a membrane valve which has a valve body in which a recess is constructed which is closed by an elastic membrane to form a valve chamber in which a valve seat is arranged, the front face of which faces the membrane. In the open position of the outlet valve the membrane is arranged at a distance from the valve seat, wherein a valve channel passes through the valve seat. In the closed position the membrane sits on the valve seat so that the outlet valve is closed.

The elastic membrane of the pump chamber and the elastic membrane of the outlet valve can be a common membrane of the membrane pump device. However, separate membranes can also be provided.

To achieve a constant low flow rate, regulation of the liquid flow is necessary. However, such a regulation has proved to be particularly difficult in the development of a membrane pump device the outlet valve of which is a membrane valve. In tests it has been found that the system tends to oscillate.

A prerequisite of the invention is that in the rest position a pressing pressure is applied to the membrane of the outlet valve by an actuating device so that the membrane closes the valve channel. For example, the pressure can be applied by a spring-loaded ram.

In the membrane pump device according to the invention the regulating properties are improved decisively in that the outward flow path comprises a first outward flow channel which connects the outlet opening of the pump chamber to an inlet opening of the valve chamber of the outlet valve, and comprises a second outward flow channel which connects the outlet valve channel to the exit connection, wherein the cross-section area of the outlet valve seat is smaller than the cross-section area of the region of the outlet valve chamber surrounding the outlet valve seat. This arrangement effects a "mechanical negative feedback", which is advantageous for regulating the fluid flow.

At the start of the pump stroke the fluid in the pump chamber is under pressure. Since the pump chamber is in fluid connection with the inlet opening of the valve chamber of the outlet valve via the first outward flow channel, the outer area of the membrane which surrounds the valve seat is subjected to pressure by the fluid. The inner area of the membrane, on the other hand, is not charged with pressure, since the membrane sits with the inner area on the valve seat. With the pump stroke the spring force of the spring-loaded ram which presses the membrane on to the valve seat must be overcome. As soon as the membrane is lifted off the valve seat, the inner area of the membrane is also subjected to pressure by the fluid. Since the inner area of the membrane is smaller than the outer area, however, which results from the fact that the cross-section area of the outlet valve seat is smaller than the cross-section area of the region of the valve chamber surrounding the valve seat, the force with which the membrane is pressed by the valve seat increases only slightly due to the relatively low change in the effective area, so that, as the pump pressure decreases, the restoring force of the spring-loaded ram rapidly predominates again. It has been found in tests that the system does not tend to oscillate then.

The form of the valve seat is not decisive for the opening properties of the outlet valve. A preferred embodiment of the invention provides for an annular valve seat for the valve seat of the outlet valve.

The construction of the inlet valve is not decisive for the opening properties of the outlet valve. A preferred embodiment of the invention provides for a membrane valve also as the inlet valve, wherein both valves are preferably of the same construction. The inlet valve preferably has an inlet valve body in which a recess is constructed which is closed by an elastic membrane to form an inlet valve chamber in which an inlet valve seat is arranged, the front face of which faces the membrane and in the open position of the inlet valve is arranged at a distance from the membrane, wherein an inlet valve channel passes through the inlet valve seat. The pump chamber and inlet and outlet valve can in turn have a common elastic membrane.

In a preferred embodiment the membrane pump device or a part of the membrane pump device is constructed as a cassette intended for a single use, which is intended for use with an actuating device for the membrane pump. However, the construction of the membrane pump device or of a part thereof as a disposable cassette is not essential for the opening properties of the outlet valve. The membrane pump device and actuating device can also be devices which cannot be separated from one another in use.

In a particularly preferred embodiment the pump chamber body and the inlet valve and outlet valve body are a constituent of a one-component or multi-component housing body of the cassette, wherein the membrane of the pump chamber and the membrane of the inlet and outlet valve are arranged on a mounting surface which can be coupled to an assembly surface of the actuating device.

The membrane pump according to the invention comprises the pump device according to the invention and an actuating device which is constructed such that the membrane of the pump chamber becomes deformable between a suction configuration and a discharge configuration, wherein the inlet and outlet valve can be alternately opened and closed so that fluid can be conveyed by the membrane pump.

The advantages of the invention are evident in particular in a membrane pump of which the actuating device preferably has an outlet adjusting device which has an outlet control element for deforming the membrane of the outlet valve, which is spring-loaded in a rest position in which the membrane of the outlet valve sits on the outlet valve seat, so that the outlet valve is closed, wherein the outlet control element can be moved out of the rest position into a functioning position in which the membrane of the outlet valve is arranged at a distance from the outlet valve seat so that the outlet valve is opened.

For actuating the inlet valve the actuating device preferably has a corresponding inlet adjusting device which has an inlet control element for deforming the membrane of the inlet valve, which is spring-loaded in a rest position in which the membrane of the inlet valve sits on the inlet valve seat, so that the inlet valve is closed, wherein the inlet control element can be moved out of the rest position into a functioning position in which the membrane of the inlet valve is arranged at a distance from the inlet valve seat so that the inlet valve is opened.

The actuating device furthermore preferably has a first working fluid line for supplying the inlet adjusting device with a working fluid for actuating the inlet control element and a second working fluid line for supplying the outlet adjusting device with a working fluid for actuating the outlet control element, and the inlet adjusting device preferably has a first working fluid valve for influencing a cross-section of the first working fluid line and the outlet adjusting device has a second working fluid valve for influencing a cross-section of the second working fluid line, wherein the second working fluid valve is configured as a proportional valve and the first working fluid valve is configured as a switching valve.

A particularly preferred embodiment provides that the actuating device has a control device, with which the first and second working fluid valve are connected electrically, wherein the control device is configured such that an intended pressure value for the second working fluid valve is determined as a function of the fluid mass flow of the membrane pump device such that the fluid mass flow is constant during the discharge phase of the membrane pump device.

The actuating device preferably has a control chamber and a control fluid line for charging the control chamber with a control fluid, in which a control fluid valve which is constructed for changing a cross-section of the control fluid line is arranged, wherein the membrane of the pump chamber is deformable into a suction configuration or a discharge configuration by charging with the control fluid. For determining the fluid mass flow a control fluid pressure sensor which is connected electrically to the control device is preferably provided, wherein the control device is configured such that the fluid mass flow is determined as a function of the pressure signal of the control fluid pressure sensor.

The membrane pump can advantageously be used in medical technology. However, advantages also emerge during use in other technology sectors. A particularly preferred use is the use of the membrane pump in a blood treatment apparatus, in particular dialysis apparatus, with a container for providing a medical liquid, in particular an anticoagulation solution.

An embodiment of a membrane pump which comprises a pump device and an actuating device is described in detail in the following.

Figure 2:
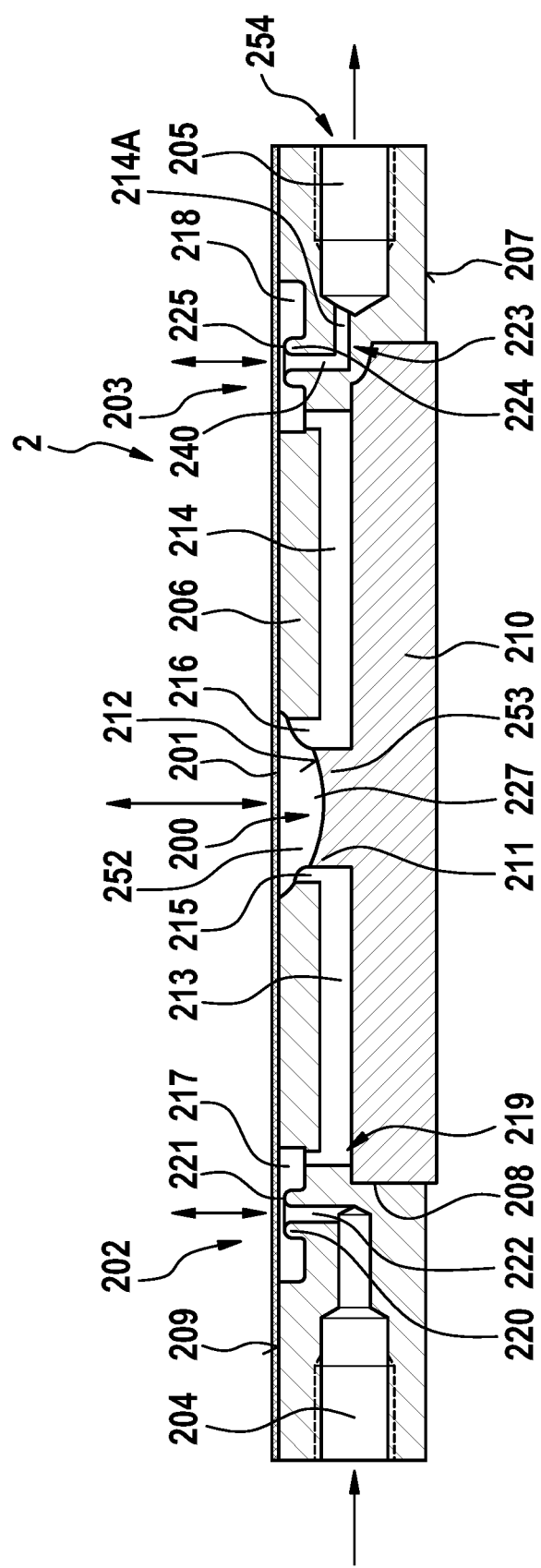
Figure 3:
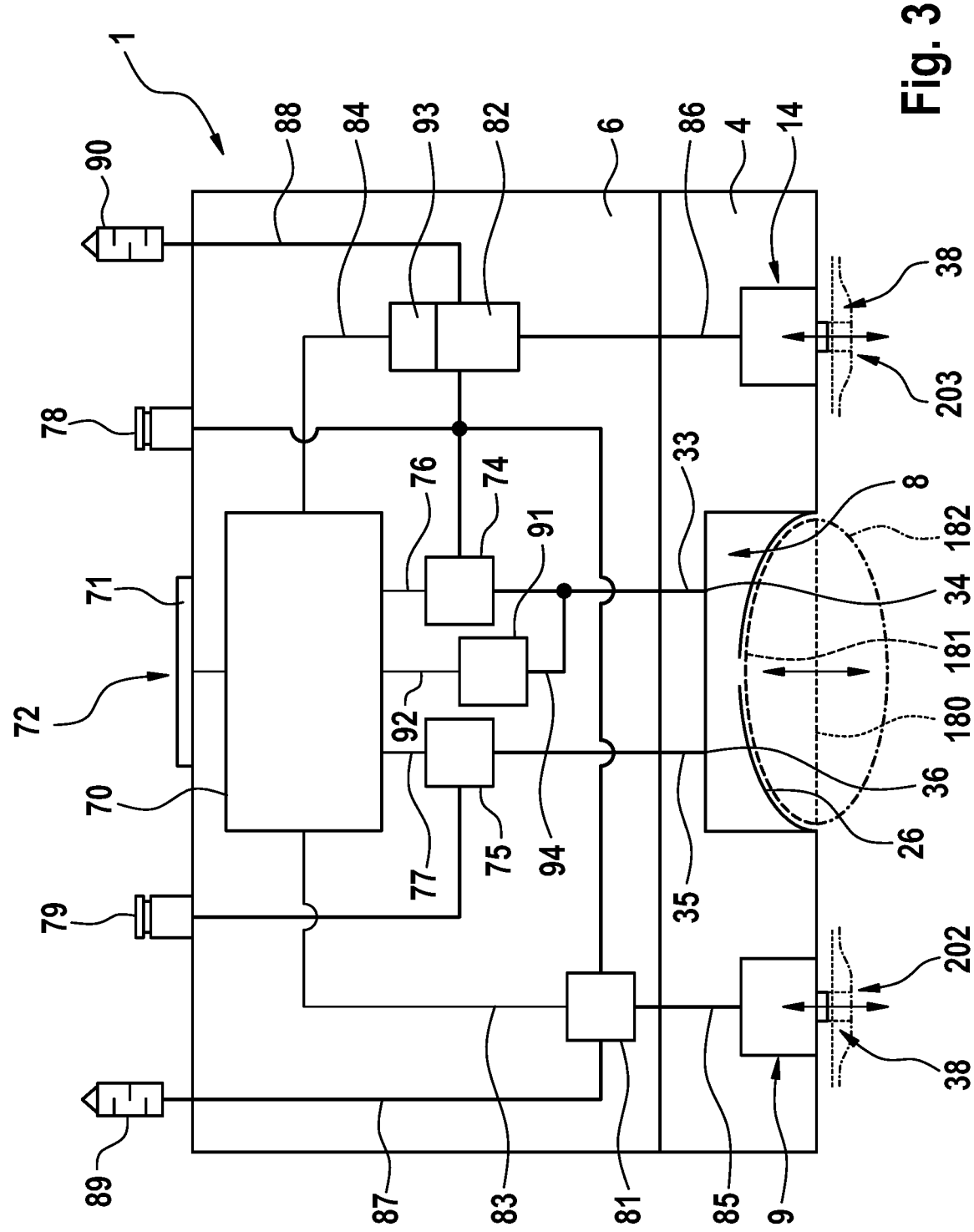
Figure 4:
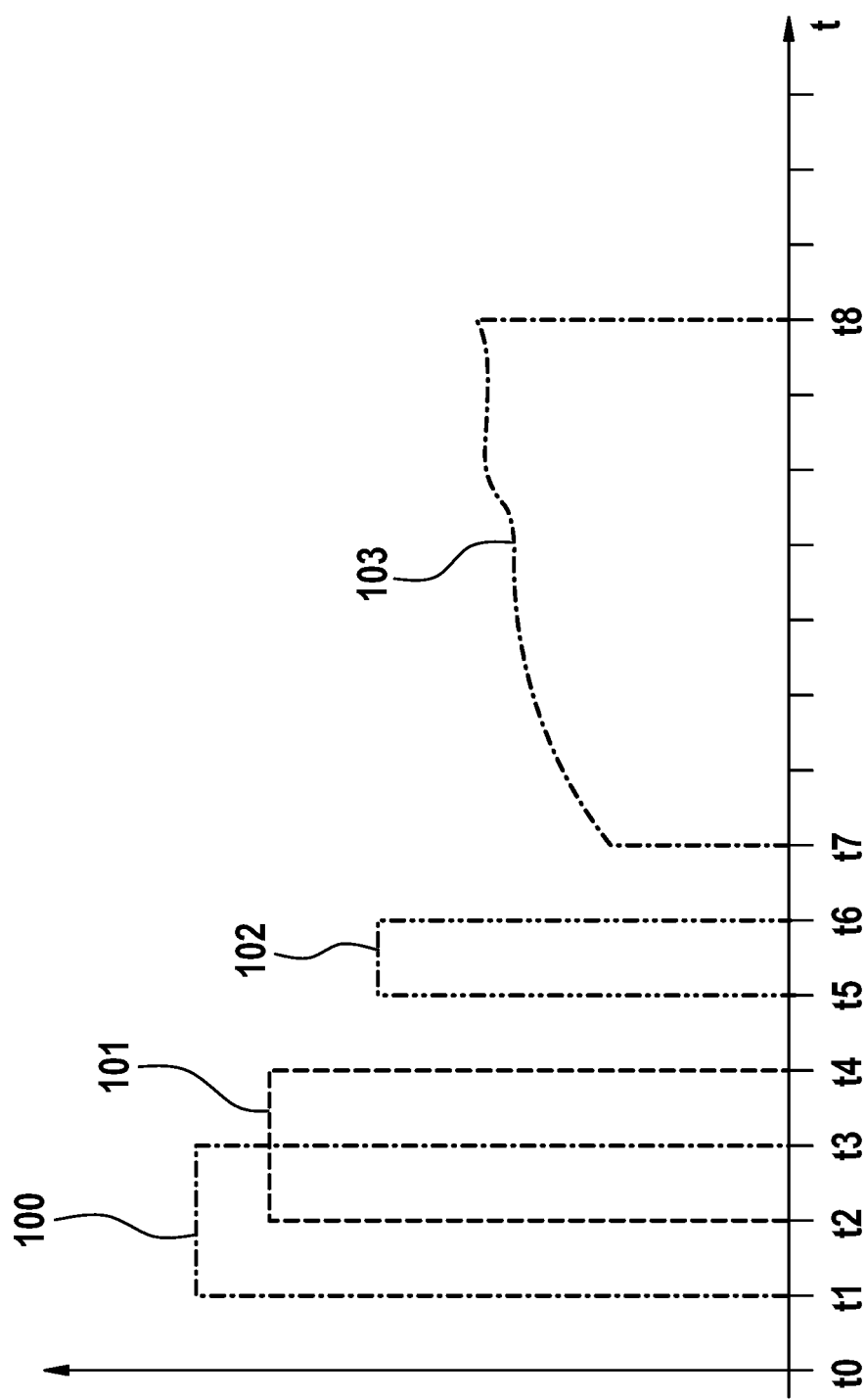
Figure 5:
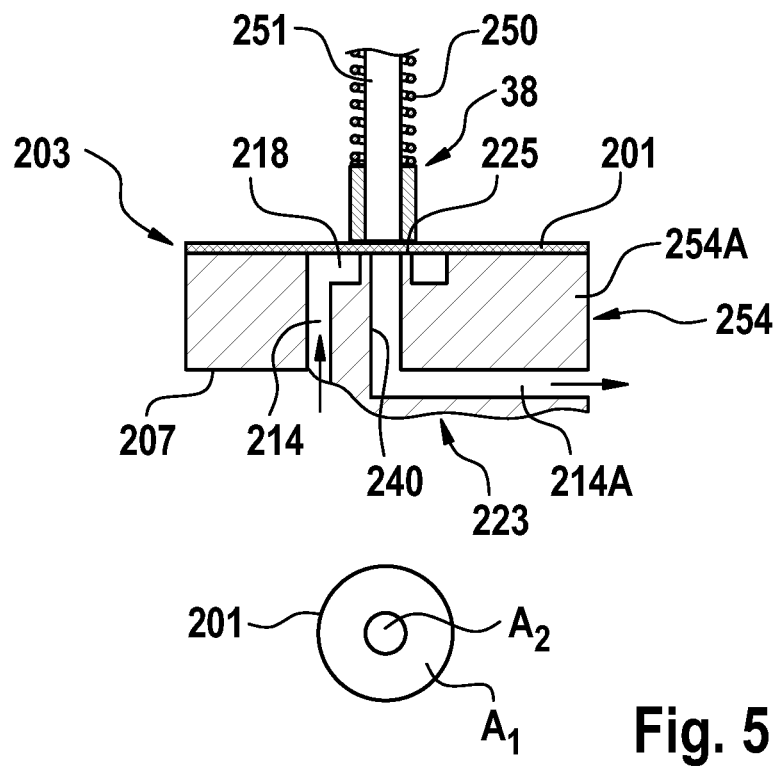
Figure 6:
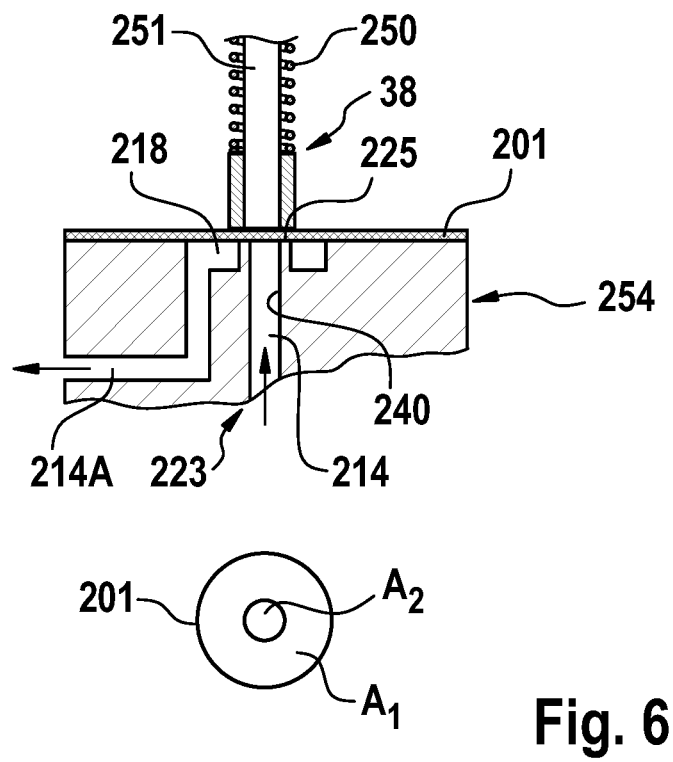
Figure 7A:
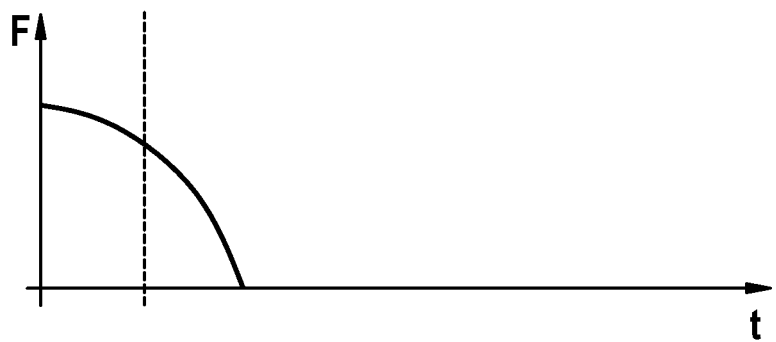
Figure 7B:
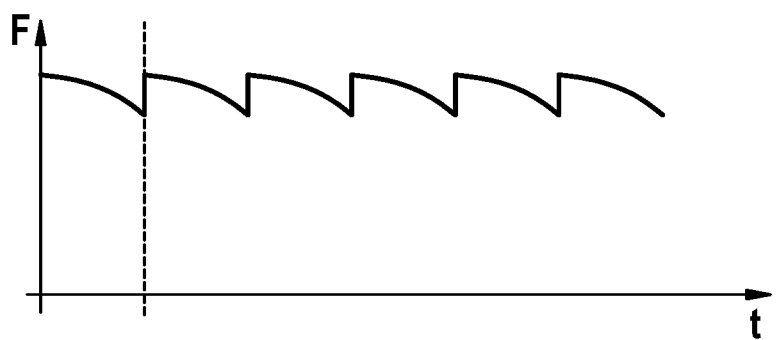
Figure 7C:
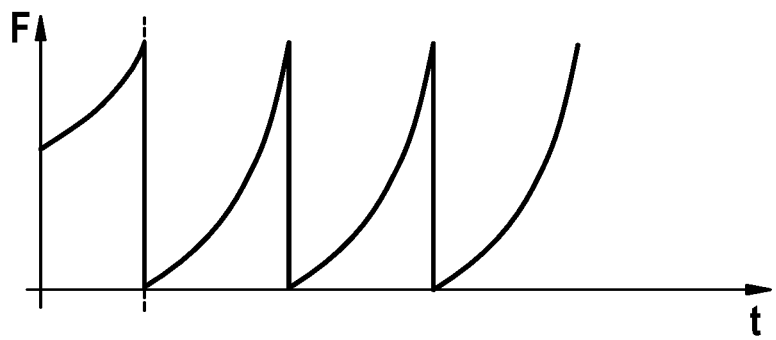
Figure 8A:
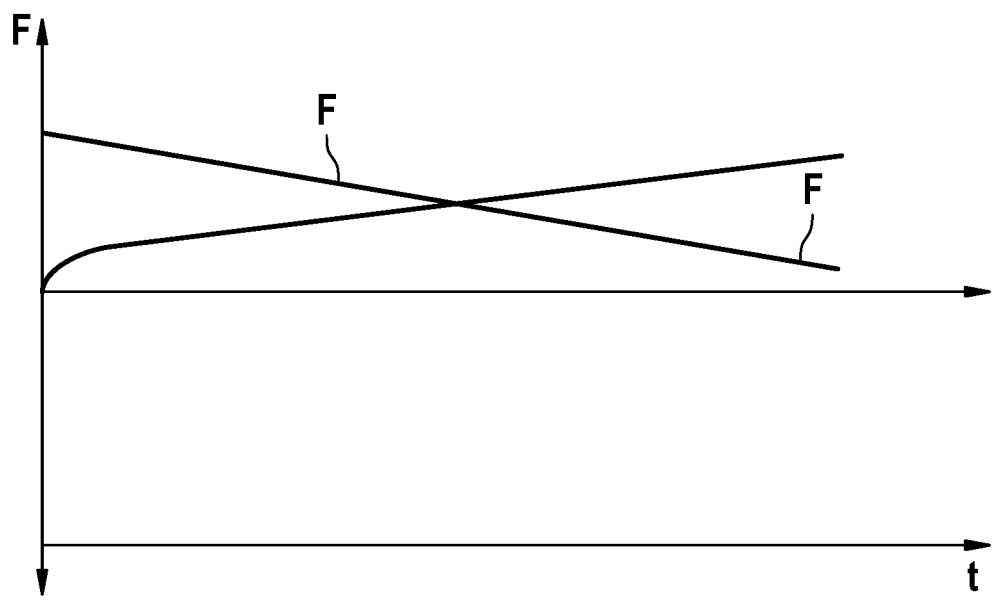
Figure 8B:
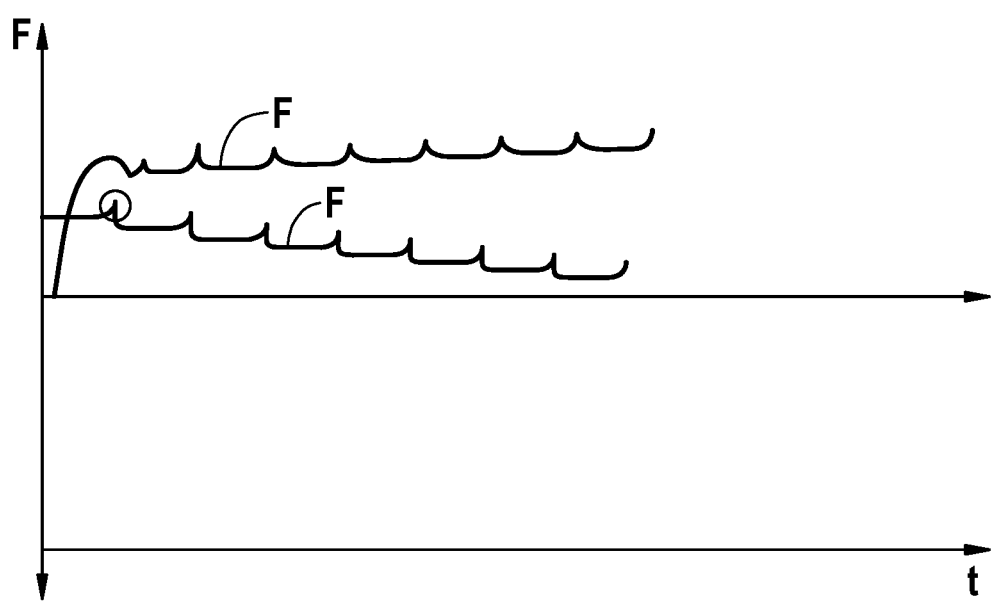

The figures show:

FIG. 1 a section of a part of an actuating device with a control chamber and an adjusting device, FIG. 2 a section of a membrane pump device, FIG. 3 a flow diagram of the actuating device according to FIG. 1, FIG. 4 a control diagram for the actuating device according to FIG. 1 and FIG. 5 a diagram of the outlet valve according to the invention, FIG. 6 a diagram of another outlet valve arrangement, FIG. 7A the force acting on the outlet valve in the opening direction in the outlet valve according to the invention with regulation, FIG. 7B the force acting on the outlet valve in the opening direction in the outlet valve according to the invention without regulation, FIG. 7C the force acting on the outlet valve in the opening direction in another outlet valve arrangement, FIG. 8A the course with respect to time of the forces in the case of a "mechanical negative feedback" and FIG. 8B the course with respect to time of the forces in the case of a "mechanical positive feedback".

An embodiment of the membrane pump according to the invention which has an actuating device and a membrane pump device is first described with reference to FIGS. 1 to 4, wherein all the assemblies of the membrane pump are described in detail.

The components of the membrane pump which are particularly essential for the invention are described with reference to FIGS. 5 and 6 and FIGS. 7A to 7C with the aid of diagrams of the outlet valve and with the aid of the course with respect to time of the force acting on the membrane of the valve in the opening direction compared with another outlet valve arrangement.

The actuating device 1 shown in FIG. 1 is provided for the mechanical activation of a membrane pump device 2 shown in FIG. 2, wherein a mechanical interconnection, not shown, of the actuating device 1 and the membrane pump device 2 renders possible a conveying of fluid of a preferably liquid fluid with complete separation of the fluid to be conveyed from the actuating device 1.

The actuating device 1 is shown according to the diagram of FIG. 1 purely by way of example with mirror symmetry about a mirror plane which is aligned perpendicularly to the plane of the diagram of FIG. 1 and which comprises a central axis 3. The actuating device 1 comprises a base body 4, which is rectangular-shaped in construction by way of example and can be produced in particular as an injection moulding of plastic. On an upper side 5, constructed flat by way of example, of the base body 4 a control assembly 6 which is described in more detail in the following in connection with FIG. 3 is mounted. An underside, at least substantially flat in construction by way of example, of the base body 4 serves as an assembly surface 7 for the membrane pump device 2 shown in FIG. 2 and likewise described below in more detail.

As can be seen from the part section of FIG. 1, a control chamber 8 and an adjusting device 9 are arranged in the base body 4. In this context the control chamber 8 is provided for actuating a membrane 201 of a membrane pump 200 which is constructed in the membrane pump device 2. The adjusting device 9 serves to activate a membrane valve 202, 203 which is likewise constructed in the membrane pump device 2.

The control chamber 8 is constructed by way of example as a rotationally symmetric recess in the assembly surface 7, wherein the central axis 3 is provided as a rotational axis for a profile of the control chamber 8. The control chamber 8 is substantially provided with a bowl-shaped cross-section and has a circular base region 10, a wall region 11 shaped like a cone section, an annular contact surface 12 and adjacent thereto an outflow region 15 shaped like a cone section. The base region 10 is formed by way of example by a surface of an annular sealing element 16 which is inserted in a recess 17 adjacent to the control chamber 8 and which has an L-shaped profile with respect to the central axis 3. The sealing element 16 lies with a circular cylindrical outer surface 18 flat on an opposite inner surface, not shown, of the recess 17 and has on a shorter L arm an annular shoulder 19 facing radially inwards, which is provided for sealing contact on an outer surface of a channel part 20 constructed rotationally symmetric about the central axis 3. In order to ensure unambiguous placing of the sealing element 16 and the channel part 20 the recess 17 has an annular shoulder 21 projecting radially inwards, on which an axial, annular front face 22 of the sealing element 16 lies with positive locking. The channel part 20 in its turn lies with a step 23 on the front face 22. A central recess 24, 25 passes through both the sealing element 16 and, respectively, the channel part 20 and are to be regarded as a constituent of a control fluid line 33.

In the control chamber 8 a shaped body 26 is accommodated which, purely by way of example is constructed rotationally symmetrically about the central axis 3 and comprises a main body 27 configured substantially as a spherical shell section, an annular shoulder 28 protruding radially outwards from this and a supporting ring 29 aligned coaxially to the central axis 3. A centrally arranged recess 30 passes through the main body 27 which forms a mounting surface 31 shaped like a spherical calotte on a surface facing away from the supporting ring 29.

The annular shoulder 28 is adjacent to the contact surface 12 of the control chamber 8, while the supporting ring 29 is supported on the base region 10 of the control chamber 8 on the front face. The mounting surface 31 serves as a demarcation for a spatial section which is called the membrane working region 32 and when the membrane pump device 2 is mounted on the actuating device 1 limits a deformation of the membrane 201 of the membrane pump 200. The recess 30 in the shaped body 26 serves as a control fluid opening 34.

Adjacent to the control chamber 8 the adjusting device 9, which by way of example is a linear actor which can be operated by fluid, is arranged in the base body 4. By way of example, the adjusting device 9 comprises a control element 38 which is accommodated in a linearly movable manner in a recess 37 and is provided for actuation of the membrane valve 202, 203 of the membrane pump device 2. The control element 38 is displaced by way of example into a rest position, not shown, by the action of a spring, not shown, without provision of pressurised fluid. According to the diagram of FIG. 1, the control element 38 is in a functioning position by provision of pressurised fluid. The control element 38 comprises a cylindrical ram 39, the longitudinal axis 40 of which is aligned transversely to the assembly surface 7. The ram 39 is mounted with a rear end region on a connecting plate 41 and is fixed with a front end region 42 on a sealing membrane 43 constructed in the shape of a plate. The connecting plate 41 is constructed in the shape of a circular disc purely by way of example and has on a front side 44 on which the ram 39 is mounted centrally an annular supporting ring 45 in a region lying radially outwards, which protrudes in the same direction as the ram 39. As can be seen from the diagram of FIG. 1, the supporting ring 45 has a U-shaped cross-section with a centrally arranged, circumferential groove 46 and with a convexly curved supporting surface 47 facing away from the front side 44 adjacent to a sealing ring 48.

The sealing ring 48 is constructed coaxially to the ram 39 and rotationally symmetrically to the longitudinal axis 40 and has an annular sealing bead 49, 50 lying radially inwards and, respectively, lying radially outwards. The sealing bead 49 lying radially inwards is accommodated in a groove-shaped, circumferential depression 51 in the base body 4 and is fixed on the base body 4 purely by way of example by a threaded ring 52 which is screwed on to a screw neck 54 of the base body 4 constructed coaxially to the longitudinal axis 40 and provided with a recess 53 for the ram 39. In the same manner the sealing bead 50 lying on the outside is likewise fixed on the base body 4 by a threaded ring 55 which is screwed with an external thread 56 into an internal thread 57 constructed on the base body 4.

In a region between the inner sealing bead 49 and the outer sealing bead 50 an annular recess 60 is incorporated in the base body 4 opposite the supporting ring 45, which renders possible a linear movement of the control element 38 along the longitudinal axis 40 and according to the diagram of FIG. 1 downwards. The sealing ring 48 fixed in a sealing manner on the base body 4 determines, together with the annular recess 60, a working space which represents an end region of a working fluid channel 58 and can be supplied with pressurised fluid. During such supplying of this working space the control element is displaced out of a rest position, not shown, into the functioning position according to FIG. 1 due to an elastic deformation of the sealing ring 48. By this means the sealing membrane 43 is also deformed, and can be brought out of a position protruding from the assembly surface 7 into the position according to FIG. 1 which is at least substantially flush with the surface. It is provided here that in the rest position the sealing membrane 43 is adjacent to the particular assigned membrane valve 202, 203 of the membrane pump device 2, in order to bring the membrane valve 202, 203 out of an open position into a closed position. When the working space is charged with pressurised fluid, due to the associated displacement of the control element 38 into the functioning position according to FIG. 1 a opening movement 30 for the particular assigned membrane valve 202, 203 of the membrane pump device 2 takes place, as is also shown in diagram form in FIG. 3.

The sealing membrane 43 has on an upper side 61 facing the ram 39 an annular shoulder 62 which is provided with a projection 63 facing radially inwards which engages by positive locking into an annular groove 64 constructed on the front end region 42. By this positive locking connection between the ram 39 and the sealing membrane 43 a bidirectional transmission of force from the ram 39 to the sealing membrane 43 and vice versa is rendered possible. In a circumferential region lying radially outwards on the sealing membrane 43 this is provided with a coaxially protruding holding ring 65 formed as one piece, which is fixed non-positively in an annular groove 66 incorporated in the base body 4 in a groove-like manner coaxially to the longitudinal axis 40, so that the sealing membrane 43 ensures fluid separation between the moving space 59 and the surroundings of the actuating device.

FIG. 2 shows in purely diagram form a section of a membrane pump device 2 which is constructed for coupling to the actuating device 1 and which can be used for conveying a fluid, which is provided at an entry connection 204, to an exit connection 205. By way of example, the membrane pump device 2 comprises a rectangular base plate 206 which is provided from an underside 207 with a recess 208. The recess 208 is at least to the greatest extent filled with a closing plate 210 which is mounted from the underside 207 and has in a central region facing away from the underside 207 a supporting projection 211 which extends in the direction of the upper side 209 and which has a concave, in particular calotte shell-shaped form on a front face 212 facing away from the underside 207. A pump chamber 252 is thereby formed in a pump chamber body 253, which is part of the housing body 254 of the pump device 2. The recess 208 in the base plate 206 is constructed such that after assembly of the closing plate 210 into the base plate 206 a groove-like inward flow channel 213 and a groove-like outward flow channel 214 are formed, which each open out at discharge openings 215, 216 adjacent to the supporting projection 211 in the direction of the upper side 209. At an end region facing away from the supporting projection 211 the inward flow channel 213 opens into a valve chamber 217, constructed cylindrically by way of example, of a first membrane valve 202, and in the same manner the outward flow channel 214 opens at an end region facing away from the supporting projection 211 into a valve chamber 218, constructed cylindrically by way of example, of a second membrane valve 203.

The first membrane valve 202 is provided as an inlet valve for influencing an inward flow path 219 which comprises the entry connection 204, the valve chamber 217 and the inward flow channel 213. For this, a valve seat 220 of annular construction, the front face 221 of which is arranged at a distance from the upper side 209 of the base plate 206 and through which a valve channel 222 passes centrally, is arranged in the valve chamber 217. In contrast, the fluid-communicating connection between the valve chamber 217 and the inward flow channel 213 is realised in a region of the valve chamber 217 lying radially outwards.

The second membrane valve 203 is provided as an outlet valve for influencing an outward flow path 223 which comprises the exit connection 205, the valve chamber 218 and the outward flow channel 214. For this, a valve seat 224 of annular construction through which a valve channel 240 passes centrally is arranged in the valve chamber 218. The front face of the valve seat 224 is arranged at a distance from the upper side 209 of the base plate 206. The valve seat 224 is surrounded concentrically by the valve chamber, wherein the outward flow channel 214 connects the discharge opening 216 of the membrane pump 200, i.e. the outlet opening thereof, to the valve chamber 218. The fluid-communicating connection between the valve chamber 218 and the exit connection 205 is realised in a region of the valve chamber 218 lying radially outside. The outward flow path 223 comprises, in addition to the first outward flow channel 214 leading to the outlet valve 203, a second outward flow channel 214A which leads away from the outlet valve 203 and is connected to the valve channel 240. The second outward flow channel 214A connects the valve channel 240 to the exit connection 205.

Purely by way of example, the entire upper side 209 of the base plate 206 is covered with a rubber-elastic membrane 201 which is fixed, for example, by material locking to the upper side 209 and therefore ensures fluid separation between the valve chambers 217, 218 and the surroundings of the membrane pump device 2. The membrane 201 furthermore also serves to separate a pump chamber 227 demarcated by the recess 208 and by the supporting projection 211 and the membrane 201 from the surroundings of the membrane pump device 2.

When the membrane pump device 2 is mounted on the actuating device 1, with the aid of the first adjusting device 9 shown in FIG. 1, for example, a deformation of the membrane 201 can be carried out via the valve seat 220 in order thereby to press the membrane 201 on to the front face 221 of the valve seat 220 to form a local seal, and therefore to interrupt a fluid-communicating connection between the entry connection 204 and the inward flow channel 213. Furthermore, with the aid of a second adjusting device 9 (14) in mirror image to that shown in FIG. 1, which for clarity is not shown in FIG. 1, a deformation of the membrane 201 can be carried out via the valve seat 224 in order thereby to press the membrane 201 on to the front face 225 of the valve seat 224 to form a local seal and therefore to interrupt a fluid-communicating connection between the first outward flow channel 214 and the exit connection 205.

Furthermore, in the region of the pump chamber 227 above the supporting projection 211 the membrane 201 can be brought by suitable charging of the recess 30 with control fluid or a reduced pressure out of the neutral position shown in FIG. 2 into a convex suction configuration, shown purely in diagram form in FIG. 3, or into a concave discharge configuration, shown purely in diagram form in FIG. 3.

As already stated above, the actuating device 1 shown in FIG. 3 is divided purely by way of example into the base body 4 and the control assembly 6, wherein the components contained in the base body 4 have already been described comprehensively above in connection with FIG. 1.

The control assembly 6 comprises a control device 70 which can be constructed, for example, as a microprocessor or microcontroller and is constructed to execute a definable process programme. By way of example, it can be provided that the control device 70 can be brought via an interface 71 into electrical connection with a higher-level control device, not shown, which can be, for example, a programmable control, so that the higher-level control device can provide a control command to the control device 70. Alternatively, it can be provided that the control device 70 can operate self-sufficiently without external commands and activate the components described in more detail below in a suitable manner. These components are on the one hand a control fluid arrangement 72 for providing control fluid to the control chamber 8 and on the other hand a working fluid arrangement 73 for providing working fluid to the two adjusting devices 9, 14, shown in diagram form, which are called the inlet adjusting device 9 and outlet adjusting device 14.

The control fluid arrangement 72 comprises a first control fluid valve 74 and a second control fluid valve 75, which by way of example can each be constructed as solenoid valves and which are connected electrically via control leads 76, 77 to the control device 70. The first control fluid valve 74 is in fluid-communicating connection via the first control fluid line 33 which opens into the control chamber 8 with a first control fluid opening 34. Furthermore, the first control fluid valve 74 is in fluid-communicating connection with a first control fluid connection 78 and renders possible an elective release or blocking of a fluid-communicating connection between the first control fluid connection 78 and the first control fluid opening 34.

The second control fluid valve 75 is in fluid-communicating connection via the second control fluid line 35 which opens into the control chamber 8 with a second control fluid opening 36. Furthermore, the second control fluid valve 75 is in fluid-communicating connection with a second control fluid connection 79 and renders possible an elective release or blocking of a fluid-communicating connection between the second control fluid connection 79 and the second control fluid opening 36.

Preferably, it is provided that a compressed air source, not shown, is connected to the first control fluid connection 78, while a vacuum source, not shown, is connected to the second control fluid connection 79. When the membrane pump device 2 shown in FIG. 2 is mounted on the actuating device 1 shown in FIG. 3, by suitable, preferably alternate, in particular cyclically recurring, activation of the two control fluid valves 74 and 75 a sequence of pressurising and depressurising can be effected for the control chamber 8, as a result of which the membrane 201 of the membrane pump 200 can be brought out of the neutral position 180 initially into a convexly curved suction position 181 and then into a concavely curved discharge position 182. By this alternating deformation of the membrane 201 of the membrane pump 200 a delivery stroke is effected for the fluid accommodated in the membrane pump 200, so that with suitable activation of the membrane valves 202 and 203 this can be conveyed from the entry connection 204 to the exit connection 200. In order to be able to effect this activation of the two membrane valves 202 and 203, the inlet and outlet adjusting devices 9 and 14 are provided, which can each act with the assigned inlet and outlet control elements 38 on the opposite sections of the membrane 201, in order to render possible electively a sealing mounting of the membrane 201 on the particular valve seat 220, 224 or a release of the particular valve seat 220, 224.

For this purpose the inlet adjusting device 9, which purely by way of example is provided for influencing the membrane valve 202 assigned to the inward flow channel 213, comprises a first working fluid valve 81 which is connected via a control lead 83 to the control device 70 in order to render possible an electrical activation of the working fluid valve 81. Furthermore, the working fluid valve 81 is in fluid connection with the first control fluid connection 78 and coupled in fluid communication via a first working fluid line 85 to the first adjusting device 9. The working fluid valve 81, which can be in particular a 3/2-way solenoid valve, accordingly can electively effect supplying of the inlet adjusting device 9 with pressurised working fluid or venting of the adjusting device 9, wherein the venting takes place via a first venting channel 87 to a first sound absorber 89.

When the sealing membrane 43 is in a neutral position in which the sealing membrane is deflected downwards, the sealing membrane presses the membrane 201, which can be mounted underneath, of the membrane pump device 2 on to the valve seat 220, as a result of which the inward flow channel 213 is closed. As can be seen from the diagram in FIG. 1, charging of the first adjusting device 9 with pressurised fluid leads to an adjusting movement of the ram 39 in the working space 58, as a result of which the sealing membrane 43 is brought out of the neutral position into a functioning position in which the sealing membrane 43 is at least almost level with the housing, so that the membrane 201 of the membrane pump device 2 is lifted up from the valve seat 220 due to its elasticity properties, so that the inward flow channel 213 is released. The outlet adjusting device 14, which purely by way of example is provided for influencing the membrane valve 203 assigned to the outward flow channel 214, comprises a second working fluid valve 82 which is connected via a control lead 84 to the control device 70 in order to render possible an electrical activation of the working fluid valve 82. Furthermore, the working fluid valve 82 is in fluid connection with the first control fluid connection 78 and coupled in fluid communication via a second working fluid line 86 to the outlet adjusting device 14. The working fluid valve 82, which can be in particular a 3/3-way piezo pressure regulator valve, accordingly can electively effect supplying of the second adjusting device 14 with pressurised working fluid or venting of the second adjusting device 14, wherein the venting takes place via a second venting channel 88 to a second sound absorber 90.

As can be seen from the diagram of FIG. 1, charging of the outlet adjusting device 14 with pressurised fluid leads to an adjusting movement of the ram 39, as a result of which the sealing membrane 43 which is deflected downwards in a neutral position in FIG. 1 and presses the membrane 201, which can be mounted underneath, of the membrane pump device 2 on to the valve seat 224, as a result of which a blocking effect is caused for the outward flow channel 214, can be brought into a functioning position in which the sealing membrane 43 is at least almost flat, as is shown in FIG. 1, and as a result of which the membrane 201, which can be mounted underneath, of the membrane pump device 2 is lifted up from the valve seat 224 due to its elasticity properties and releases the outward flow channel 214.

For regulating the pressure in the control chamber 8 a pressure sensor 91 is provided, which is connected electrically via a sensor lead 92 to the control device 70 and which purely by way of example is in fluid-communicating connection with the first control fluid line 33 by means of a fluid line 94. By this means the pressure sensor 91 can determine the fluid pressure present in the control chamber 8 and transmit this as an electrical signal to the control device 70 via the sensor lead 92.

By way of example, the second working fluid valve 82 is additionally assigned a pressure sensor 93 which, purely by way of example, is integrated into the second working fluid valve 82 and is connected electrically to the control device 70 via the assigned second control lead 84.

FIG. 4 shows in strictly diagram form a model of the flow of the activating signals 101 to 104 which are provided for activating the individual components of the actuating device 1 of the control device 70. In this context neither the signal levels nor the time sections are selected to scale.

At a time t0 no activating signal is emitted by the control device 70. The two adjusting devices 9, 14 are therefore each in a rest position in which the assigned control element 38 allows the particular sealing membrane 43 to protrude from each assembly surface 7 and a deformation of the membrane of the particular opposite membrane valves 202, 203 is therefore ensured. This can be seen from FIG. 3 with the aid of the dot-dash membrane of the membrane valves 202, 203. At this point in time both the inward flow channel 213 and the outward flow channel 214 are therefore blocked.

At a time t1 the control device 70 emits an activating signal 100 for the first working fluid valve 81, as a result of which this is switched from a venting position into an aerating position and pressurising of the inlet adjusting device 9 takes place. Due to the pressurising, the ram 39 of the inlet adjusting device 9 moves out of the neutral position according to FIG. 3, in which the sealing membrane 43 protrudes from the assembly surface 7 and the membrane, shown by the dot-dash line in FIG. 3, of the assigned membrane valve 202 is deformed, into a functioning position, as shown by the broken line in FIG. 3. As a result of this the membrane valve 202, which can be mounted opposite, of the membrane pump device 2 is opened, as is shown by the broken line in FIG. 3, and renders possible at least in principle an inward flow of fluid from the entry connection 204 into the membrane pump 200.

At a time t2 the control circuit 70 emits an activating signal 101 to the second control fluid valve 75, as a result of which this is switched from a blocking position into a release position and depressurising of the control chamber 8 takes place. By this depressurising, the membrane 201 of the membrane pump 200 is sucked into the control chamber 8 and lies on the mounting surface 31 of the shaped body 26, so that it assumes the convexly curved suction position 181. At this point in time the pump chamber 227 of the membrane pump 200 has a maximum volume, wherein in the course of the deformation of the membrane 201 the fluid to be conveyed is sucked from the entry connection 204 into the pump chamber 227.

At a time t3 the control circuit 70 switches off the activating signal 100 for the first working fluid valve 81, as a result of which this is switched out of the aerating position into the venting position and the pressurising of the inlet adjusting device 9 is ended. As a result the ram 39 of the inlet adjusting device 9 moves, in particular due to a spring action of a restoring spring, not shown, out of the functioning position shown in FIG. 1 into a neutral position protruding from the assembly surface 7, as is shown by the dot-dash line in FIG. 3, so that the membrane valve 202, which can be mounted opposite, of the membrane pump device 2 is closed. At this point in time t3 the inward flow channel 213 in the membrane pump device 2 is blocked and escape of fluid from the pump chamber 227 of the membrane pump 200 is prevented.

At a point in time t4 the activating signal 101 is switched off by the control circuit 70 so that the second control fluid valve 75 assumes the blocking position again and the control chamber 8 initially has a constant reduced pressure from this point in time t4.

At a time t5 the control circuit 70 emits an activating signal 102 to the first control fluid valve 74, as a result of which this is switched from a blocking position into a release position and pressurising of the control chamber 8 takes place. By this pressurising the fluid accommodated in the membrane pump 200 is additionally placed under pressure. Preferably, the pressure in the control chamber 8 is such that during a subsequent discharge operation a complete deformation of the membrane 201 of the membrane pump 200 from the convexly curved suction position 181 into the concavely curved discharge position takes place, so that a maximum amount of fluid can be conveyed with the aid of the membrane pump 200.

At a point in time t6 the activating signal 102 is switched off by the control circuit 70, so that the first control fluid valve 74 assumes the blocking position again.

At a point in time t7 the control circuit 70 provides an activating signal 103 for the second working fluid valve 82, so that this can perform a regulated adjusting movement of the ram 39 associated with the outlet adjusting device 14. In this context the activating signal 103 is calculated as a function of pressure signals from the pressure sensor 91 in the control circuit 70 with the aid of an observer algorithm, in order, for example, to effect as constant as possible a fluid mass flow from the membrane pump 200 to the exit connection 205.

The position of the ram 39 accordingly changes dynamically during the fluid conveying operation, wherein the membrane valve 203 is operated in the manner of a proportional valve. Due to the increased pressure in the control chamber 8 the fluid in the pump chamber 227 of the membrane pump 200 is pushed to the exit connection 205, and this operation preferably persists until the membrane 201 lies flat on the front face 212 of the supporting projection 211 and the pump chamber 227 is therefore at least almost completely emptied.

At a point in time t8 the control circuit 70 switches off the activating signal 103, so that at this point in time the conveying operation for the membrane pump 200 is ended and a new conveying operation can begin.

FIG. 5 shows a diagram of the outlet valve 203 according to the invention, wherein the individual components of the valve 203 are labelled with the same reference symbols as in FIGS. 1 to 4. This outlet valve arrangement with the feed and removal lines is called a valve arrangement with a "mechanical negative feedback".

In the diagram the outlet adjusting device 14 with the outlet control element 38 is shown by a ram 251, which is preloaded with a spring 250, which exerts a pressing force F on the elastic membrane 201 of the outlet valve 203. The ram exerts a force F on the membrane which corresponds to the difference between the pressing force $F_F$ of the spring and a force $F_S$ which can be exerted by the outlet adjusting device 14 against the spring force on the ram 251 in order to lift the ram off from the outlet valve seat 225. The spring 250 holds the ram 251 in the rest position in which the outlet valve 203 is closed, i.e. the ram presses the membrane 201 on to the valve seat 225. In FIG. 5 the outlet valve 203 is shown in the rest position. In the functioning position the ram does not press the membrane on to the valve seat, so that the outlet valve is opened.

The valve chamber 218 of the outlet valve 203 is constructed in a valve body 254A which is part of the housing body 254 of the pump device 2. The outward flow path 223 comprises a first outward flow channel 204 which leads from the pump chamber 252 to the valve chamber 218 of the outlet valve 203, and a second outward flow channel 204A which leads from the outlet valve channel 240 to the exit connection 205. The cross-section area of the outlet valve seat 225 and of the outlet valve channel 240 is smaller than the cross-section area of the region of the outlet valve chamber 218 surrounding the outlet valve seat 225. The outer area $A_1$ of the membrane 201 which surrounds the valve seat is consequently greater than the inner area $A_2$ of the membrane 201 which lies on the valve seat 225, which is illustrated in FIG. 5.

At the start of the pump stroke the fluid in the pump chamber 252 is under pressure. Since the pump chamber 252 is in fluid connection with the valve chamber 225 of the outlet valve 203 via the first outward flow channel 204A, the outer area $A_1$ of the membrane 201 which surrounds the valve seat 225 is subjected to pressure by the fluid. A force $F_1$ which corresponds to the product of the pressure p of the fluid and the outer area $A_1$ of the membrane 201 therefore acts on the outer surface $A_1$ of the membrane 201. The inner area $A_2$ of the membrane 201, on the other hand, is not subjected to pressure, since the membrane still lies with the inner area on the valve seat, which corresponds to the rest position of the outlet valve.

During the pump stroke the ram 251 is raised from the inflowing fluid against the pressing force of the spring 250, wherein after opening of the outlet valve 203 the pressure p of the inflowing fluid decreases. At the start of the pump stroke the spring force of the ram 251, which presses the membrane 201 on to the valve seat 225, must first be overcome. This force is overcome by a force which corresponds to the product of the pressure p of the fluid and the outer area $A_1$ of the membrane being exerted on the ram by the fluid. As soon as the membrane is lifted off the valve seat, the inner area $A_2$ of the membrane 201 is also subjected to pressure by the fluid. Since the inner area $A_2$ of the membrane is smaller than the outer area $A_1$, however, the force with which the membrane is pressed by the valve seat increases only slightly due to the relatively small change in the effective area, so that, as the pump pressure decreases, the restoring force of the spring-loaded ram rapidly predominates again. The outlet valve 203 therefore manifests on opening a behaviour which requires an ever increasing actuating force on the ram as the pump stroke progresses, in order to continue to convey constantly.

FIG. 6 shows as a comparative example another outlet valve arrangement in which the outward flow path 223 comprises a first outward flow channel 214 which connects the outlet opening of the pump chamber 252 to the outlet valve channel 240, and comprises a second outward flow channel 214A which connects the outlet valve chamber 218 to the exit connection 205, wherein the cross-section area of the outlet valve seat 225 is smaller than the cross-section area of the region of the valve chamber 218 surrounding the valve seat. This case is called "mechanical positive feedback". In such an arrangement, when the membrane 201 is lifted off the valve seat the change in the effective area is greater than in the case of "mechanical negative feedback". The dynamic pressure on lifting off the membrane consequently acts on a very much larger area. Due to this significantly greater change in the effective area, the force exerted on the ram by the fluid predominates. The outlet valve therefore manifests on opening a behaviour which requires an ever decreasing actuating force on the ram as the pump stroke progresses, in order to continue to convey constantly. This is in contradiction to the concept that a force must first be built up in order to lift the ram off the valve seat. It has been found that such a valve arrangement tends towards a non-regulatable behaviour. Oscillations have been found in tests.

FIG. 7A shows for the outlet valve arrangement according to the invention (FIG. 5) the course with respect to time of the force acting on the ram 251 in the opening direction for the case where regulation of the flow of liquid such as is described with reference to FIGS. 1 to 4 does not take place.

It is found that the force drops relatively rapidly to zero. FIG. 7B shows in the outlet valve arrangement according to the invention (FIG. 5) the course with respect to time of the force acting on the ram in the opening direction with regulation of the flow of liquid described with reference to FIGS. 1 to 4, in order to ensure a constant flow rate, while FIG. 7C shows the force acting on the ram in the opening direction as a function of time for the case of "mechanical positive feedback" (FIG. 6). In contrast to the case of "mechanical positive feedback" (FIG. 6), a clearly uniform course is found for the case of "mechanical negative feedback" (FIG. 5). In the case of "mechanical positive feedback" (FIG. 6), a periodic increase and decrease in the force between a maximum value and zero is found.

The differences described above between a "mechanical negative feedback" and a "mechanical positive feedback" are explained again with reference to FIGS. 8A and 8B.

The forces opening the valve can be divided into the two contents $F_S$ (control fluid) and $F_A$ (working fluid). A flow results when the spring force $F_F = F_S + F_A$. This is the state in which no pressing force is exerted on the valve seat.

FIG. 8A shows for the case of "mechanical negative feedback" the course of the forces $F_F$, $F_S$, $F_A$ with respect to time. During the "mechanical negative feedback" the forces $F_S$ and $F_A$ counteracting the spring force $F_F$ increase and, respectively, decrease. During a pump stroke the force $F_S$ increases monotonously and the force $F_A$ decreases monotonously. Since the regulation allows $F_S$ to increase monotonously, a uniform continuous flow is generated.

FIG. 8A shows the case of "mechanical positive feedback" in which due to the area ratios described above a brief increase in the force $F_A$ is found on opening of the valve. This increase in force must then be compensated by the regulating system by means of a lowering of the pressure in the control chamber of the drive. The regulator lowers $F_S$ to the extent that the valve closes again. The course of the forces $F_A$ and $F_S$ with respect to time does not run monotonously during the pump stroke. The flow changes constantly between "high flow" and "no flow".

The invention claimed is:

1. A membrane pump device for conveying fluids and comprising:
   an actuating device;
   at least one elastic membrane;
   a pump chamber body in which a recess, that is closed by the at least one elastic membrane to form a pump chamber, is constructed;
   an inward flow path that connects an entry connection to an inlet opening of the pump chamber;
   an outward flow path that connects an outlet opening of the pump chamber to an exit connection;
   an inlet valve provided in the inward flow path for influencing a flow of liquid in the inward flow path; and
   an outlet valve provided in the outward flow path for influencing a flow of liquid in the outward flow path, wherein
   the outlet valve is a membrane valve that has an outlet valve body in which a recess is constructed that is closed by the at least one elastic membrane to form an outlet valve chamber in which an outlet valve seat is arranged,
   a front face of the outlet valve seat faces the at least one elastic membrane and, in the open position of the outlet valve, is arranged at a distance from the at least one elastic membrane,
   an outlet valve channel passes through the outlet valve seat, the outward flow path comprises a first outward flow channel that directly connects the outlet opening of the pump chamber to the outlet valve chamber in a state in which the at least one elastic membrane closes the outlet valve channel and comprises a second outward flow channel that connects the outlet valve channel to the exit connection, the second outward flow channel is closable with the at least one elastic membrane, a cross-sectional area of the outlet valve seat is smaller than a cross-sectional area of a region of the outlet valve chamber surrounding the outlet valve seat, the actuating device is configured to deform the at least one elastic membrane between a suction configuration and a discharge configuration, the actuating device comprising an outlet adjusting device that has an outlet control element for deforming the at least one elastic membrane, the outlet control element comprising a spring-loaded ram that comprises a spring and a ram, the outlet control element being spring-loaded in a rest position wherein the at least one elastic membrane is deformed to sit on the outlet valve seat so that the outlet valve is closed, and the outlet control element is configured to be moved out of the rest position into a functioning position by a force of liquid against the at least one elastic membrane, which overcomes a force of the spring, such that the at least one elastic membrane is arranged at a distance from the outlet valve seat so that the outlet valve is open.

2. The membrane pump device according to claim 1, wherein the outlet valve seat is an annular valve seat.

3. The membrane pump device according to claim 1, wherein the inlet valve is a membrane valve which has an inlet valve body in which a recess is constructed that is closed by the at least one elastic membrane to form an inlet valve chamber in which an inlet valve seat is arranged, wherein a front face of the inlet valve seat faces the at least one elastic membrane and, in the open position of the inlet valve, is arranged at a distance from the at least one elastic membrane, wherein an inlet valve channel passes through the inlet valve seat, and wherein the inward flow path comprises a first inlet flow channel, that directly connects the entry connection to the inlet valve channel, and comprises a second inlet flow channel that connects the inlet valve chamber to the inlet opening of the pump chamber, and the second inlet flow channel is closable with the at least one elastic membrane.

4. The membrane pump device according to claim 3, wherein the inlet valve seat is an annular valve seat.

5. The membrane pump device according to claim 3, wherein the membrane pump device, other than the actuating device, is constructed as a cassette intended for a single use.

6. The membrane pump device according to claim 5, wherein the pump chamber body and the inlet valve body and the outlet valve body are constituents of a one-component or multi-component housing body of the cassette, wherein the at least one elastic membrane is arranged on a mounting surface that is configured to be coupled to an assembly surface of the actuating device.

7. The membrane pump device according to claim 3, wherein the inlet and outlet valves are capable of being alternately opened and closed so that fluid can be conveyed by the membrane pump device.

8. A blood treatment apparatus comprising a container for providing a medical liquid, and a membrane pump device according to claim 7 for conveying the medical liquid.

9. The blood treatment apparatus of claim 8, wherein said blood treatment apparatus is a dialysis apparatus.

10. The blood treatment apparatus of claim 8, wherein the medical liquid is an anticoagulation solution.

11. The membrane pump device according to claim 1, wherein the actuating device has an inlet adjusting device that has an inlet control element for deforming the at least one elastic membrane, the inlet control element being spring-loaded in a rest position wherein the at least one elastic membrane sits on the inlet valve seat so that the inlet valve is closed, wherein the inlet control element is configured to be moved out of the rest position into a functioning position in which the at least one elastic membrane is arranged at a distance from the inlet valve seat so that the inlet valve is open.

12. The membrane pump device of claim 1, wherein said fluids are medical liquids for blood treatment.

13. A membrane pump device for conveying fluids, comprising:
an actuating device;
at least one elastic membrane;
a pump chamber body in which a recess, that is closed by the at least one elastic membrane to form a pump chamber, is constructed;
an inward flow path that connects an entry connection to an inlet opening of the pump chamber;
an outward flow path that connects an outlet opening of the pump chamber to an exit connection;
an inlet valve provided in the inward flow path for influencing a flow of liquid in the inward flow path; and
an outlet valve provided in the outward flow path for influencing a flow of liquid in the outward flow path,
wherein
the outlet valve is a membrane valve that has an outlet valve body in which a recess is constructed that is closed by the at least one elastic membrane to form an outlet valve chamber in which an outlet valve seat is arranged,
a front face of the outlet valve seat faces the at least one elastic membrane and, in the open position of the outlet valve, is arranged at a distance from the at least one elastic membrane,
an outlet valve channel passes through the outlet valve seat,
the outward flow path comprises a first outward flow channel that directly connects the outlet opening of the pump chamber to the outlet valve chamber in a state in which the at least one elastic membrane closes the outlet valve channel and comprises a second outward flow channel that connects the outlet valve channel to the exit connection,
the second outward flow channel is closable with the at least one elastic membrane,
a cross-sectional area of the outlet valve seat is smaller than a cross-sectional area of a region of the outlet valve chamber surrounding the outlet valve seat,
the inlet valve is a membrane valve that has an inlet valve body in which a recess is constructed that is closed by the at least one elastic membrane to form an inlet valve chamber in which an inlet valve seat is arranged, a front face of the inlet valve seat faces the at least one elastic membrane and, in the open position of the inlet valve, is arranged at a distance from the at least one elastic membrane, an inlet valve channel passes through the inlet valve seat, the inward flow path comprises a first inlet flow channel, that directly connects the entry connection to the inlet valve channel, and comprises a second inlet flow channel that connects the inlet valve chamber to the inlet opening of the pump chamber, the second inlet flow channel is closable with the at least one elastic membrane, the actuating device is constructed such that the membrane of the pump chamber is deformed between a suction configuration and a discharge configuration, the inlet and outlet valves are capable of being alternately opened and closed so that fluid can be conveyed by the membrane pump, the actuating device has an outlet adjusting device that has an outlet control element for deforming the at least one elastic membrane, which is spring-loaded in a rest position in which the at least one elastic membrane sits on the outlet valve seat so that the outlet valve is closed, the outlet control element is configured to move out of the rest position into a functioning position in which the at least one elastic membrane is arranged at a distance from the outlet valve seat so that the outlet valve is open, the actuating device has an inlet adjusting device that has an inlet control element for deforming the at least one elastic membrane, the inlet control element is spring-loaded in a rest position wherein the at least one elastic membrane sits on the inlet valve seat so that the inlet valve is closed, the inlet control element is capable of being moved out of the rest position into a functioning position in which the at least one elastic membrane is arranged at a distance from the inlet valve seat so that the inlet valve is open, the actuating device has a first working fluid line for supplying the inlet adjusting device with a working fluid for actuating the inlet control element, and a second working fluid line for supplying the outlet adjusting device with a working fluid for actuating the outlet control element, and the inlet adjusting device has a first working fluid valve for influencing a cross-section of the first working fluid line and the outlet adjusting device has a second working fluid valve for influencing a cross-section of the second working fluid line, wherein the first working fluid valve is constructed as a switching valve and the second working fluid valve is constructed as a proportional valve.

14. The membrane pump device according to claim 13, wherein the actuating device has a control device, with which the first and second working fluid valves are connected electrically, wherein the control device is configured such that an intended pressure value for the second working fluid valve is determined as a function of a fluid mass flow of the membrane pump device such that the fluid mass flow is constant during a discharge phase of the membrane pump device.

15. The membrane pump device according to claim 14, wherein the actuating device has a control chamber and a control fluid line for charging the control chamber with a control fluid, in which a control fluid valve, which is constructed for changing a cross-section of the control fluid line, is arranged, wherein the at least one elastic membrane is deformed into the suction configuration or the discharge configuration by charging the control chamber with the control fluid.

16. The membrane pump device according to claim 15, wherein a control fluid pressure sensor is connected electrically to the control device and the control device is configured such that a fluid mass flow is generated as a function of a pressure signal of the control fluid pressure sensor.

* * * * *